United States Patent [19]

Cushman

[11] Patent Number: 5,255,117
[45] Date of Patent: Oct. 19, 1993

[54] ADVANCED EYE OR SENSOR PROTECTION AND HIGH SPEED VARIABLE OPTICAL ATTENUATION SYSTEM

[75] Inventor: William B. Cushman, Pensacola, Fla.

[73] Assignee: The United States of America as represented by the Secretary of the Navy, Washington, D.C.

[21] Appl. No.: 842,287

[22] Filed: Feb. 14, 1992

[51] Int. Cl.$^5$ .......................... G02F 1/26; G02B 5/30
[52] U.S. Cl. .................... 359/234; 359/236; 250/233; 2/432
[58] Field of Search ............... 359/234, 235, 236, 610; 250/232, 233; 2/432

[56] References Cited

U.S. PATENT DOCUMENTS

| | | | |
|---|---|---|---|
| 3,480,347 | 11/1969 | Walter et al. | 359/610 |
| 3,521,940 | 7/1970 | Heckman | 359/610 |
| 3,807,659 | 4/1974 | Winfrey | 359/610 |
| 4,165,919 | 8/1979 | Little | 350/236 |
| 4,279,474 | 7/1981 | Belgorod | 359/234 |
| 4,462,661 | 7/1984 | Witt | 2/432 |
| 4,511,225 | 4/1985 | Lipson | 2/432 |
| 4,524,271 | 6/1985 | Parker | 250/233 |
| 4,595,262 | 6/1986 | Ogle et al. | 250/233 |

*Primary Examiner*—Nelson Moskowitz
*Attorney, Agent, or Firm*—A. David Spevack; William C. Garvert

[57] ABSTRACT

In order to protect the eyes or other sensor, from light produced, e.g., by modern laser weapons which have extremely fast onset times and high power per pulse, a protective shutter device is provided which is based on the integrative property of such sensors. The sensor is shielded for a large proportion of the time and only exposed after a light detector associated with the protective device has assured a safe environment. The normal exposure provided is a series of rapid image-views that integrate over time within the sensor. In an eye goggles embodiment, clear vision is maintained and a fast-response variable-density "sunglass" is perceived by the wearer. Only one eye is exposed and thus at risk at any one time, and that eye only about 10% of the total time. A high-speed mechanical shutter controls the exposure experienced by the sensor.

10 Claims, 8 Drawing Sheets

TO POWER SUPPLY

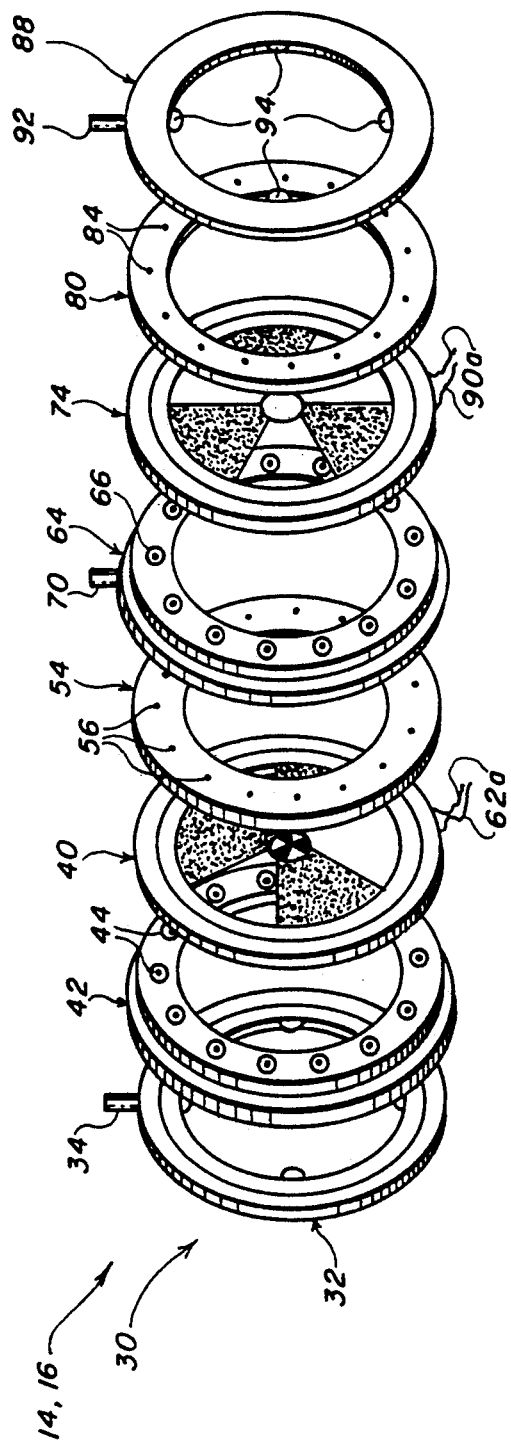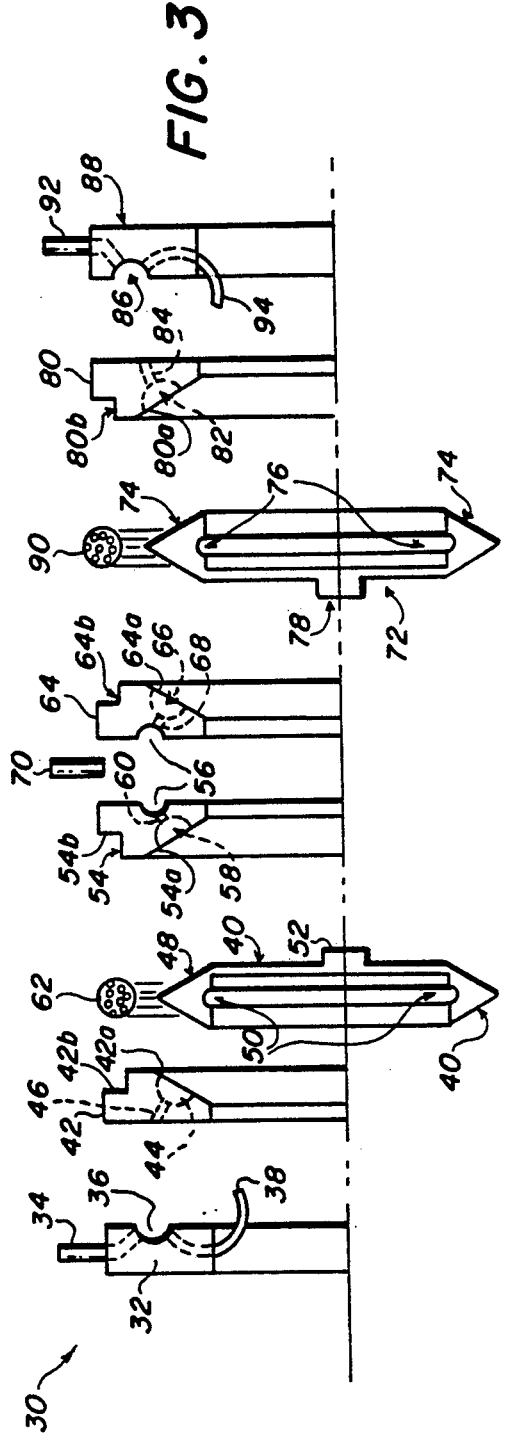

ADVANCED EYE OR SENSOR PROTECTION AND HIGH SPEED VARIABLE OPTICAL ATTENUATION SYSTEM

BACKGROUND OF THE INVENTION

1. Field of the Invention

The present invention relates to protection devices for the eyes or other optical sensors and more particularly, to a device for protecting an eye or optical-sensor from intense light sources, such as a laser or atomic blast, which can have extremely rapid rise times and be of an unknown wavelength or of multiple wavelengths.

2. Description of the Prior Art

High powered light sources, and, in particular, lasers, are being used increasingly in industry and within the military for many applications. In the industrial community, lasers may pose an extreme threat to workers using them. This threat is usually controlled or neutralized quite easily because the laser wavelength is known and goggles or other protective apparatus with band reject filters for rejecting that particular wavelength can be used. However, even in the controlled industrial environment some processes or applications require the use of fixed multi-wavelength or variable wavelength (dye tunable) lasers, thus making eye and optical-sensor protection more difficult. In a military environment, lasers are used for targeting and rangefinding as well as in offensive applications. As a result, the eyes, and optical-sensors of all types, run an extreme risk of damage from laser light produced by "friendly" sources as well as enemy sources. Further, space reconnaissance satellites are another obvious target for laser attack.

In response to this threat, the Defense Advanced Research Projects Agency (DARPA) has initiated a program to develop methods for providing protection against laser threats. This program is currently focused on eight different approaches.

Briefly considering these approaches, one candidate involves the use of phase-transition switches. To explain, certain materials undergo drastic changes in the optical properties thereof which are associated with normal phase changes. For example, vanadium oxide is light transparent in the semi-metallic phase and highly reflective in the metallic phase. This phase transition can theoretically be induced by a slight temperature increase, such as would accompany a laser strike. Although this is an extremely promising approach to sensor protection, actual fabrication of acceptable devices has presented problems.

Self-induced gratings are also being considered. In some materials, the dielectric constant is a non-linear function of the intensity of an applied electric field and work is being done to find a material in which standing waves from a laser are able to induce sufficient dielectric change to cause the material to act as a diffraction grating and thus cause the incident energy to be scattered out of the optical path. Materials with sufficient non-linear behavior to provide protection of the type desired have not yet been identified.

Another approach is to use self-induced focusing. Non-linear optical materials can also be exploited by arranging optical paths that change focal distance as a function of light intensity. However, while this effect has been demonstrated, the effect produced by materials tested to date is not of sufficient strength to provide the protection desired.

Another approach involves scattering in a nonhomogeneous medium. Some materials change optical properties locally as a function of light intensity. For example, small spheres of a non-linear optical material can be suspended in a polymer of similar refractive index. As the light intensity increases, the dielectric constant of the spheres changes much more rapidly than the ambient, thus causing scattering. Although this approach is promising, the practical application thereof to the problem of laser light protection is limited by the lack of availability of suitable materials.

Coherence filters have also been considered and some theoretical approaches to producing a filter which can discriminate and reflect coherent light (laser light) have been proposed and demonstrated in a weak form. This approach could produce an ideal laser protection device if realized, but, at present, the technology is not available.

One way to circumvent the weak non-linear dielectric effect of existing materials is to bring the incoming energy to a focus and then apply one of the techniques listed above. For example, a unity-gain telescope could be used with a protective device located at a focal plane where the energy is concentrated. This approach can be enhanced or exanded with a microlens array. A microlens array is effectively an array of small unity-gain telescopes arranged as a goggle or protective filter. This approach also has some promise, but still depends on finding suitable non-linear optical materials or the like and has the additional drawback that the image quality is seriously degraded when presented as a series of overlapping images.

An old approach in laser protection is to provide an optical path with a sacrificial reflecting element (mirror) in the path. As energy exceeds a certain threshold, the reflecting element will "burn off," thus blocking the optical path. This approach has several disadvantages: the technology involved in the mirror design is critical (and as yet unsuccessful), the optical design is often by neccesity cumbersome in order to accommodate a reflecting surface, and once sacrified, the device is non-functional.

A technologically feasible or realizable approach to sensor protection is to substitute another sensor in the optical path. For example, a human can observe a scene via a television link and be perfectly safe. This approach certainly has advantages, with the primary one being that the technology is currently available and known to work. However, the initial sensor in the system, i.e., the vidicon camera in the example referred to is not protected at all and can be destroyed if exposed to strong laser light.

Modern laser weapons have extremely fast onset times (Q switch) and high power output per pulse. Such weapons can also emit energy at an unknown wavelength. These characteristics imply that conventional approaches to providing eye and sensor protection based on either fast, responsive switching or selective wavelength-dependent filtering are unlikely to be adequate. Moreover, the more esoteric approaches to protection discussed above are not as yet reliable enough, advanced enough or sophisticated enough to enable the use thereof in practical protective devices.

Patented devices of interest here include those disclosed in U.S. Pat. Nos. 3,245,315 (Marks et al); 4,842,400 (Klein); 4,264,154 (Petersen); 4,848,890 (Horn); 4,968,127 (Russell et al); and 4,978,208 (Hsu et al).

Briefly considering these patents, the Marks et al patent discloses eyeglasses or spectacles which are said to be capable of protecting the eyes of a wearer from damage by a blinding flash of light. A photocell controls the opening and closing of two electro-optic shutters mounted in the eyeglass frame. The shutters comprise conductive coatings or crystal plates which become darkened when the intensity of the light received by the photocells exceeds a safe level.

The Klein patent discloses eyeglasses which are designed to prevent the wearer from being blinded by excessive luminous intensity (produced, e.g., by a welding plasma). The eyeglasses include a pair of plates each having strips or zones thereon which can selectively be made opaque or transparent under the control of a scanning unit in the form of a shift register. The plate scanning frequency is preferably in excess of 16 Hz which, due to the persistence of vision, makes the scan invisible.

The Petersen patent discloses polarizing sunglasses including an arrangement for automatically controlling the transmission of light through the lenses of the glasses. An actuator incrementally rotates a polarized element in response to the brightness of the light received by a sensor through the glasses.

The Horn patent discloses an eye protection device wherein liquid crystal matrices are positioned over the eyes of a wearer and a sun-tracking photosensor determines the area of direct sunlight in the field of view of the wearer.

The Russell patent discloses eyeglasses including electronically controlled liquid crystal lens assemblies wherein the optical transmissivity thereof is automatically controlled to a level correlated to the intensity level of the ambient light as sensed by a photocell array.

The Hsu et al patent discloses eye protection goggles incorporating a pair of spatial light modulators comprising a photosensor diode and a photoemitting diode array. Each modulator has two semiconductive layers of opposite electrical polarities that are sandwiched together with layers of the same polarity (P or N) in electrical contact with each other.

Patents relating to goggles, eyeglasses, sunglasses and the like which include louvers, shutters or other movable parts for selectively blocking or modifying the light received by the eyes of a wearer include the following: U.S. Pat. Nos. 2,642,569 (Triebes et al); 2,773,411 (Schwede); 2,824,308 (Duncan); 3,689,136 (Atamian); 3,752,567 (Broadhurst); 4,386,832 (Nannini); 4,396,259 (Miller); 4,511,225 (Lipson); 4,595,262 (Ogle, deceased); 4,869,584 (Dion); and 4,953,231 (Burnett). Very briefly considering these patents, the Triebes et al patent discloses a sunguard for the eyes comprising glasses including a removable semi-opaque plate. The Schwede patent discloses glasses, including rotating optical lenses, for reducing glare. The Duncan patent discloses eyeglasses including a louvered screen. The Atamian patent discloses sunglasses with reversible shade portions. The Broadhurst patent discloses eyeglasses with interchangeable colored lenses. The Nannini patent discloses "adjustable luminous intensity" sunglasses including movable lenses. The Miller patent discloses "spectrum glasses" including a rotating color wheel. The Lipson patent discloses variable neutral density laser goggles including a rotatable polarized element. The Ogle patent discloses tunable birefringent safety goggles including a rotating polarizer. The Dion patent discloses louvered sunglasses. The Burnett patent discloses a shade attachment for eyeglasses including closeable slats.

SUMMARY OF THE INVENTION

In accordance with the invention, a device is provided which overcomes the problems of the prior art discussed above and provides effective protection for the eyes or for other optical sensors even against modern laser weapons with very rapid onset times and high power outputs per pulse, and notwithstanding the wavelength of the laser energy. The invention is in part based on the integrative property of most, if not all, sensors and provides that the sensor is shielded for a large proportion of the time (approximately 90% of the time in the case of a human eye), and only exposed after testing by an associated detector has assured the environment is safe. Exposure is provided in the form of a series of rapid image-views that integrate over time within the sensor. For example, in an embodiment wherein a laser protection eye goggle is provided, clear vision is maintained and a fast-response variable-density "sunglass" is perceived by the wearer. Only one eye need be exposed at any given time (in that the eyes are alternately exposed) and therefore, only one eye is actually at risk at any one time, and that eye only for about 10% of the total time. Such temporal integration in the human eye was first described by Bloch in 1885 (Bloch, A.M. (1885) Experience sur la vision. *Comptes Rendus de Seances de la Societe de Biologie* (Paris), Vol 37, 493-495) and the phenomenon bears his name. More recent research has shown that the human eye will integrate for about 100 msec at threshold levels of intensity (See Barlow, H.B. (1958) Temporal and spatial summation in human vision at different background intensities. *J. Physiol.* (London), Vol 141, 337-350).

The laser protection provided by the invention requires no esoteric technology such as those described above. The device of the invention uses a high-speed mechanical shutter as a basic operating element, thus providing an infinitely high extinction ratio and none of the polarization effect present in PLZT or other birefringent types of shutters.

The use of a mechanical shutter in a device where high speed is desirable might appear, at first glance, counter intuitive, even given the advantages of infinite extinction ratio and no polarization effect provided by a mechanical shutter. However, it will be shown that, in the present situation, the mechanical approach taken is, in fact, faster than similar electro-optical devices. Electro-optical approaches, for example using PLZT crystals, have turn "on" and turn "off" times in excess of 1 $\mu$s when devices of a size large enough to guarantee a good field of view are considered. Attempting to exceed this speed with higher voltages generally causes the device to be damaged. Furthermore, heating effects limit the repetition rate to relatively low frequencies, usually less than 100 Hz.

The present invention is based in part on the appreciation that a device can be rotated at an extremely high speed, using, e.g., gas bearings and a turbine drive. In fact, top rotational speed is limited only by the strength of materials used. Over fifty years ago, J. S. Beams demonstrated rotational speeds of 1,296,000 upon using the materials available at that time (Beams, J. W. "High Rotational Speeds", *J. Appl. Phy.* 8, 795-806, 1937). These materials would not have included titanium, for example, and thus, assuming only a modest increase in rotational speed due to materials advances to, say, 1.5 million rpm, this value can then be used to estimate shutter repetition rates. Assuming a three sectored shutter, the three sectors will increase the effective frequency to 3×1.5 M rpm, or 4.5 M mph, and dividing by 60 to convert to the more familiar Hz, produces a repetition rate of 75 KHz, or an increase of repetition rate over electro-optical devices by a factor of 750. In this regard, 75 KHz translates to a period of 13 μs. Given an application where the shutter is open only 10% of the time, the shutter open period is 1.30 μs. It will be seen that 1.30 μs is already much faster than a single period of an electro-optical device even ignoring the fact that electro-optic devices cannot repeat this feat without allowing some time for cooling.

The above discussion assumes a three sectored shutter, but it will be understood that shutters can be practically constructed with twice or ten times as many elements, thereby reducing the exposure time to 650 and 130 μs respectively. There is obviously a point of diminishing returns when increasing the number of shutter elements. In this regard, at 130 μs, the driving and controlling electronics would be strained to keep up. But this limit is more amenable to advances in technology than is a physical limit placed on a device by the need to dissipate heat, as in the case with electo-optics.

Accordingly, it is an object of this invention to provide an improved apparatus for eye and other sensor protection against excessive light levels.

Another object of this invention is to provide eye and other sensor protection against excessive light levels of any wavelength.

Another object of this invention is to provide eye and other sensor protection against excessive light levels with extremely rapid onset times.

Another object of this invention is to limit any potential damage that could be caused to a plurality of eyes or other sensors to only one eye or only one sensor of that plurality.

Another object of this invention is to provide a protective device incorporating an extremely high-speed shutter.

Another object of this invention is to provide a protective device including a shutter with no inherent polarization effects.

These and other objects of this invention are achieved through the provision of an optical sensor protection apparatus which comprises: a light level detecting means such as a photodiode for detecting the ambient light level; a pulse-width modulation means for producing, responsive to said detecting means, encoded binary output pulses the pulse widths of which are inversely proportional to the detected light level; at least one protective shutter; a voltage-controlled oscillator synchronized with said protective shutter at a frequency which is a multiple of the operating frequency of the protective shutter; and means responsive to the output of said light level detecting means and to the output of said voltage controlled oscillator for controlling the operating duty cycle of the protective shutter. The number of protective shutters is equal to the number of the light sensing elements (e.g., eyes in the case of goggles or glasses, or other light sensors) being protected. The protection shutters preferably comprise a plurality of disks including a plurality of sectors, and associated bearing means for supporting the disks for rotation to different positions providing different shutter openings. The apparatus preferably includes drive and braking means for controlling rotation of the disks, and position-sensing means for sensing the present disk positions and interlocking means for controlling the relation between the open and closed times of different shutters.

These and other objects, features and advantages of the invention, as well as the invention itself, will become better understood by reference to the detailed description of an exemplary embodiment of the invention found hereinbelow.

BRIEF DESCRIPTION OF THE DRAWINGS

Reference is now made to the accompanying drawings wherein like reference numerals designate identical or corresponding parts throughout the several views, and wherein:

FIG. 2 is an exploded perspective view of one of the protective shutters of FIG. 1;

FIG. 3 is a transverse cross-sectional view of the protective shutter of FIG. 2, showing for most elements only the upper half (the bottom half being identical);

DETAILED DESCRIPTION OF A PREFERRED EMBODIMENT

Figure 1:
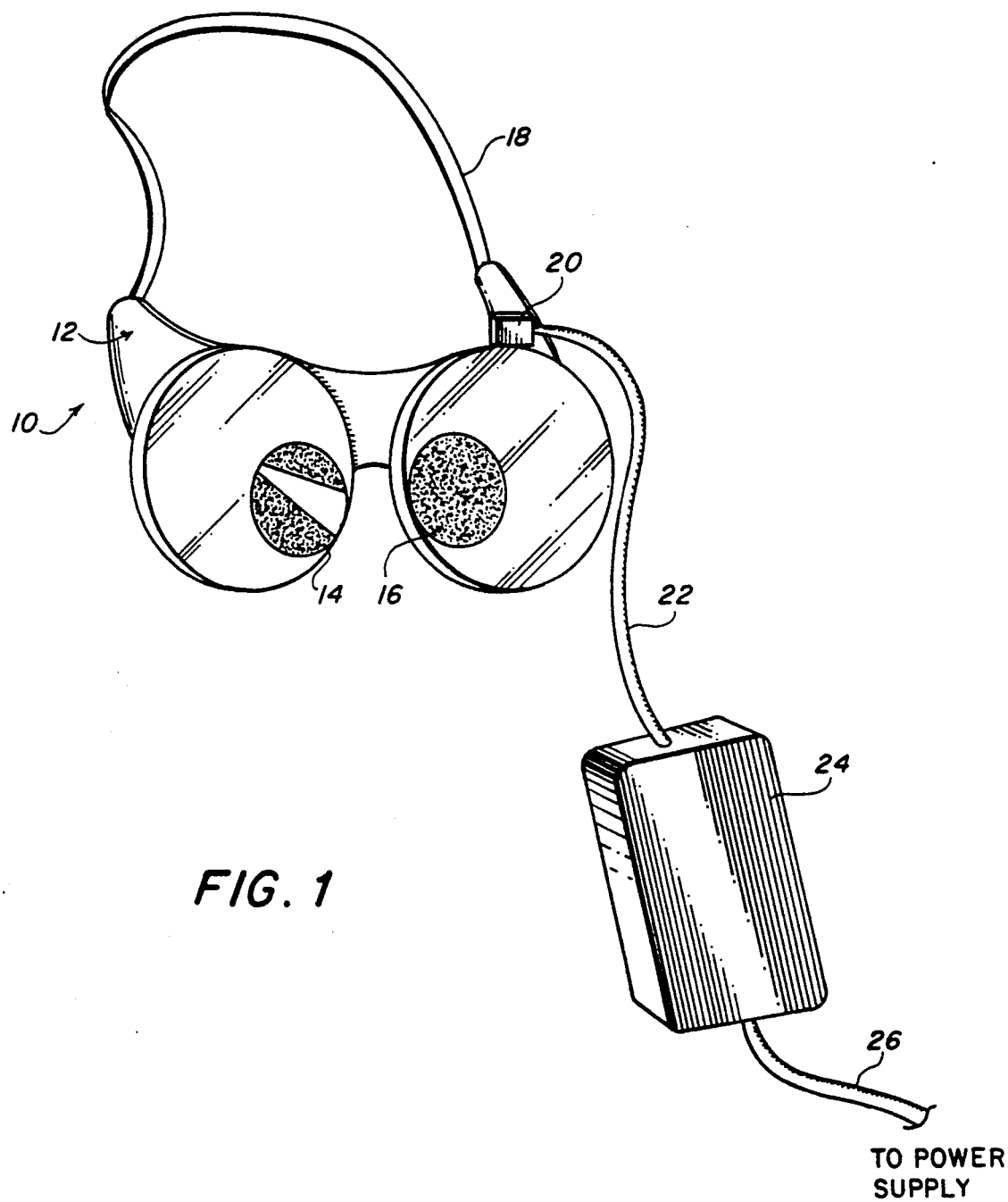
FIG. 1 is a diagrammatic perspective view of a pair of eye protection goggles, constructed in accordance with an exemplary embodiment of the invention.

Referring to FIG. 1, an eye-protection goggle apparatus in accordance with a preferred embodiment of the invention is shown. The apparatus, which is generally denoted 10, includes a frame 12 on which is mounted a pair of shutter devices or shutters 14 and 16. A strap 18 or other similar arrangement is used to hold the frame 12 and associated shutters 14 and 16 in place on the face on a wearer so that shutters 14 and 16 are respectively disposed in alignment with the eyes of the wearer. The frame 12 also supports a photosensor or photosensing unit or device 20 or other light sensing device. A connecting cord 22 is provided between the shutters 14 and 16 and a control unit or module 24 which contains a small pump (not shown) and the control circuitry (not shown) for the apparatus, and which is connected by a power supply cord 26 to a suitable source of electrical power (not shown). This apparatus protects the eyes of a wearer by providing for alternately opening protective shutters 14 and 16, with the open time of the protective shutters 14 and 16 being approximately 10% of the total time, i.e., each is open for about 10% of the time for a total for both of about 20%. This open time is inversely proportional to the amount of light falling on the eye-protection goggle apparatus 10 sensed by the photosensing unit or device 20. Further, this open time of the protective shutters 14 and 16 is reduced to zero, i.e., the shutters 14 and 16 are continuously closed, when the sensed light exceeds a predetermined level.

Referring to FIGS. 2 and 3 an exploded view is provided of one of the protective shutters (14 or 16) of FIG. 1. The shutter mechanism of FIGS. 2 and 3 includes a disk-manifold shutter assembly 30 including a rear manifold ring 32, which includes, as shown in FIG. 3, a gas inlet 34 to the manifold 36 of the rear manifold ring, and a turbine nozzle 38 which receives internal gas under pressure from the manifold 36 and directs that gas against turbine blade or inner sectored disk or wheel 40, a full cross section of which is shown in FIG. 3. A gas bearing ring 42 includes, as shown in FIG. 3, on the annular bearing face 42a thereof a plurality of depressions 44 (see also FIG. 2) with restrictive passageways 46 that allow gas from manifold 36 of rear manifold ring 32 to pressurize the depressions. The inner sectored disk or wheel 40 includes, as shown in FIG. 3, a "V" shaped bearing surface 48, turbine blades 50 and interdigitizing tabs 52 (shown in greater detail in FIG. 4 discussed below). A second gas bearing ring 54 is disposed on the opposite side of sectored disk 40 and includes one half of an air manifold 56 in communication with a plurality of depressions 58 on the annular bearing face 54a, through restrictive passageways 60 that allow gas from manifold 56 to pressurize the depressions 58. A grooved portion or area 54b of gas bearing ring 54 mates with a corresponding grooved part or area 42b of ring 42 to form a peripheral annular groove or recess which contains a rear braking coil indicated at 62 in FIG. 3 and the connecting leads 62a of which are shown in FIG. 2.

A third gas bearing ring 64 includes, as shown in FIG. 3, the other half of manifold 56 as well as a plurality of depressions 66, formed in the annular bearing face 64a, which are connected by restrictive passageways 68 to allow gas from manifold 56 to pressurize the depressions 66. A feed tube 70 shown in both FIGS. 2 and 3 provides gas pressure to manifold 56.

An outer sectored disk 72, which is similar to disk 40 but oppositely oriented as shown in FIG. 3, includes with V-shaped bearing surface 74, turbine blades 76 and interdigitizing tabs 78. Again, the construction of disks 40 and 72 is described in more detail in connection with FIG. 4.

A fourth gas bearing ring 80 includes a plurality of depressions 82 on the annular bearing face 80a thereof which are connected by respective restrictive passageways 84 to the manifold 86 of an outer manifold 88 so as to enable gas from manifold 86 to pressurize the depressions 82. Similar to the construction described above, a grooved area 80b of bearing ring 80 mates with a grooved area 64b of ring 64 to form an annular recess which contains an outer braking coil indicated at 90 in FIG. 3. The outer manifold ring 88 includes a gas inlet 92 to the manifold 86 of the outer manifold ring 88 and a turbine nozzle 94 which receives internal gas under pressure from the manifold 86 and directs that gas against turbine blades 76 of disk 72. Connecting leads for coil 90 are indicated at 90a in FIG. 2.

The basic operation of the shutter assembly of FIGS. 2 and 3 is briefly as follows: the sectored disks 40 and 72 are rotated by the turbines in gas bearings provided by gas bearing rings 42,54 and 64,80, respectively, at a high rate of speed. The relative positions of the two sectored disks 40 and 72 are controlled by braking of one disk relative to the other to effectively vary the open duty cycle, and the two sectored disks are loosely interdigitated to allow braking of the "leading" disk to provide closing of the relative opening between the sectored disks 40 and 72 until the interdigitizing tabs 52 and 78 prevent further relative movement.

It will be understood that the turbine nozzles 38 and 94 and turbine blades 50 and 76 are so arranged that both sectored disks 40 and 72 rotate in the same direction, for example, clockwise as viewed in FIG. 2. With this arrangement, braking of the outer sectored disk 72 effectively closes the shutter, and braking of the inner sectored disk 40 effectively opens the shutter.

It should also be understood that the sectored disks 40 and 72 preferably made from a conductive material, such as titanium, to enable magnetic braking, and that the rest of the shutter construction should be made, to the extent possible, from non-conductive materials for the same reason. Furthermore, the entire protective shutter assembly 30 is contained within a gas-tight construction with transparent apertures (not shown) to facilitate the use of low viscosity gases as working fluids. For example, in an application as a sensor protection device on a satellite, it is desirable to use a light and very low viscosity gas such as hydrogen as a working fluid.

Figure 4:
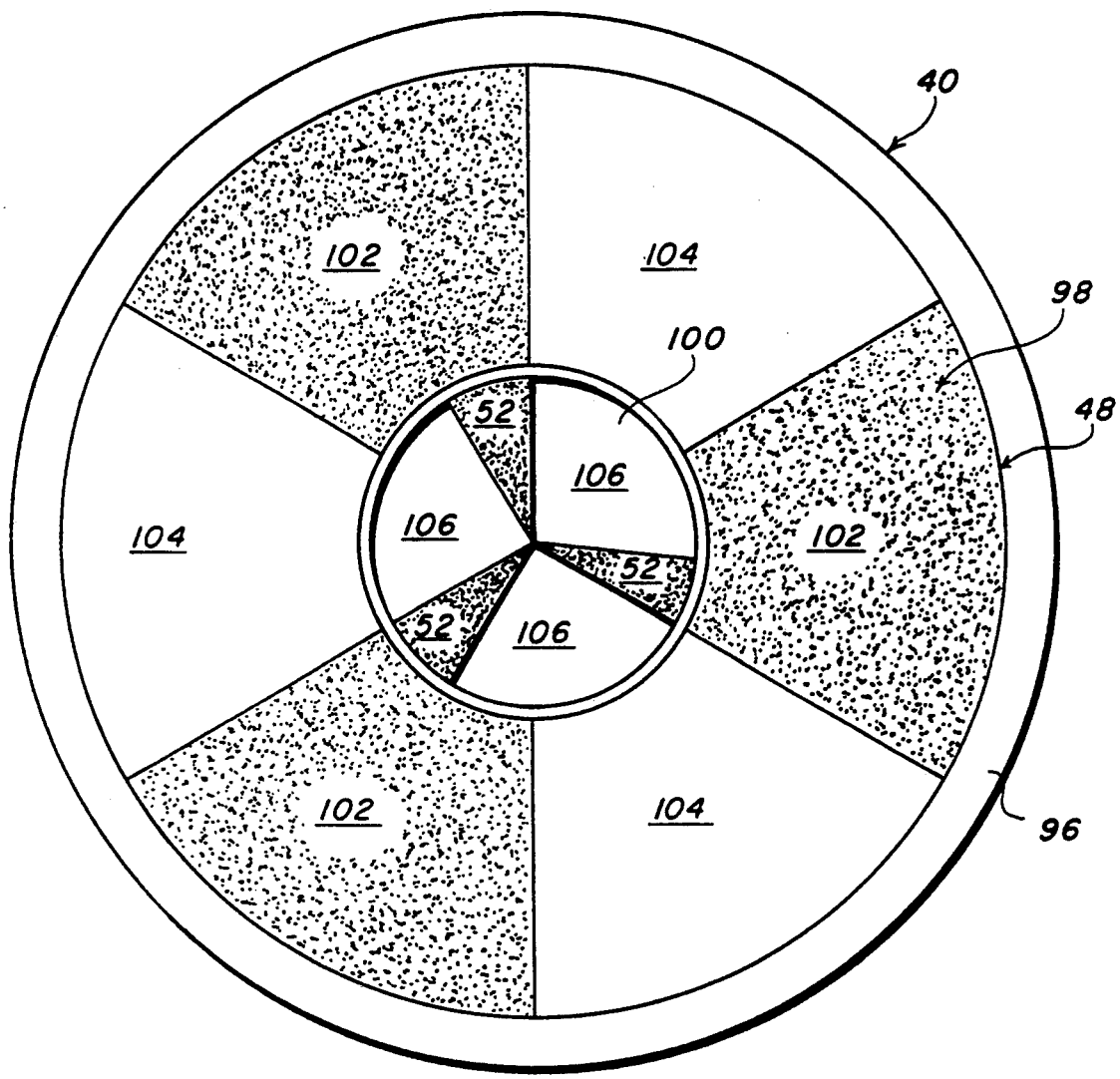
FIG. 4 is a front elevational view of one of the sectored disks of FIG. 2, showing the interdigitizing tabs.

FIG. 4 is a front elevational view of the sectored disk 40 shown in FIGS. 2 and 3. It will be appreciated that the two sectored disks 40 and 72 are substantially identical except that the turbine blades 50 and 76 are reversed on one relative to the other so that the disks 40 and 72 can both rotate in the same direction when the interdigitizing tabs 52 and 78 are interdigitized, i.e., in engagement. Referring to FIG. 4, disk 40 includes the outer V-shaped bearing surface 48 referred to above formed on an outer ring 96. A plurality of sectors 98 are disposed between outer ring 96 and an inner hub 100. The sectors 98 are alternatively opaque and transparent with the opaque sectors being denoted 102 and the transparent sectors being denoted 104. The interdigitizing tabs 52 referred to above are formed on hub 100 and stand out from the surface, i.e., are raised from the surface of hub 100 as shown in FIG. 3. The tabs 52 define corresponding recessed spaces or recesses 106 therebetween into which the corresponding interdigitizing tabs 78 from sectored disk 72 are adapted to fit. It will be understood that the opaque sectors 102 of disk 40 are somewhat larger in angular displacement than would be provided by a simple division of the circle so that there is some slight overlap of the opaque sectors of one sectored disk with those of the other. More particularly, in the embodiment shown in FIGS. 2 and 4 wherein three opaque sectors are provided, each opaque sector (e.g., sectors 102 of FIG. 4) should have an angular displacement of about 61 degrees, leaving only 59 degrees for the transparent sectors (e.g., sectors 104 of FIG. 4). The number of interdigitizing tabs is equal to the number of opaque sectors on the disk. In the preferred embodiment where there are three opaque sectors there are three interdigitizing tabs to be disposed as follows. The interdigitizing tabs corresponding to tabs 52 should each subtend 30 degrees, and be so located that when the two sectored disks 40 and 72 are locked at the closed extreme there is a 1 degree overlap of the opaque sectors from each disk (40 and 72) at each edge.

Figure 5:
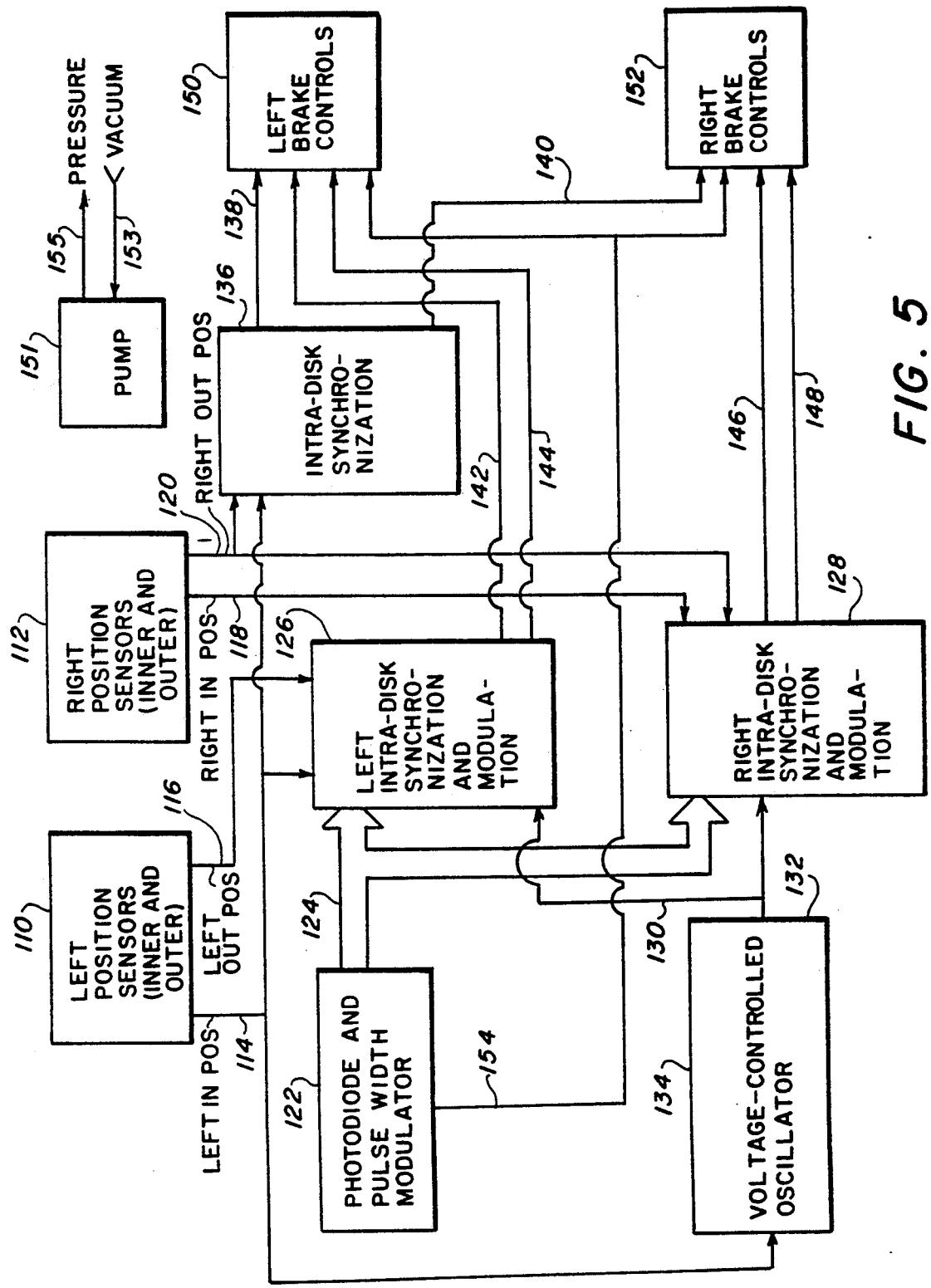
FIG. 5 is a block diagram of the control module in FIG. 1.

Referring to FIG. 5, a block diagram is provided of the control module 24 of FIG. 1. It should be understood that there are two synchronization problems to be addressed by the control module 24. First, each shutter assembly (left and right) is comprised of two disks, corresponding to disks 40 and 72, that must be synchronized while rotating at high speed. In this case, synchronization is further elaborated by controlling the relative position of the "inner" and "outer" disks 40 and 72 to effectively vary the aperture width between the disks from completely closed to wide open. Therefore, two light sensors are required for each shutter assembly in order to measure the relative position of the "inner" and "outer" sectors 40 and 72, and controlling electronics (described below) are required to maintain this intra-disk synchronization. Second, the position of each shutter 16 and 14 (left and right) must be controlled to ensure that only one shutter 14 or 16 is opened at any given time. This inter-disk synchronization is accomplished in a manner similar to the intra-disk synchronization except that in this case only one photosensor input for each shutter 14 or 16 is required. As illustrated, inner position sensor 110 and outer position sensor 112 are provided which sense the positions of the inner and outer disks (corresponding to disks 40 and 72 of shutter assembly 30 of FIGS. 2 to 4 described above) of the left and right shutter units 16 and 14 of FIG. 1, and produce corresponding outputs on lines 114,116 and 118,120, respectively.

A photodiode and pulsewidth modulator circuit 122 forming part of photosensor unit 20 of FIG. 1 produces, as the output thereof on output line 124, an eight-bit wide word representing the encoded value of the light sensed by photosensor unit 20, with the magnitude of this word being inversely proportional to the light falling on photosensing unit 20. Output line 124 is connected to left and right intra-disk synchronization and modulation circuits 126 and 128 which also receive a clock or timing input on lines 130 and 132, respectively, from a voltage controlled clock oscillator 134. The clock oscillator 134 is connected to output line 114 of left position sensor 110. As will become evident from the discussion below, this sensor input to the clock oscillator 134 causes that oscillator to be included in a phase-locked loop with the rotating disks providing the "fundamental" frequency and the output of the clock oscillator being near exactly 256 times this fundamental frequency. This higher frequency is required to control the delay of the "lagging" disk in a shutter pair corresponding to disks 40 and 72 and to thus effect "modulation." Both output lines 114 and 116 of sensors 110 are connected to left synchronization and modulation circuit 126 and both output lines 118 and 120 of input position sensors 112 are connected to right synchronization and modulation circuit 128.

The use of a phase-locked loop to control the relative position of the inner and outer disks 40 and 72 of a shutter (14 or 16) would insure synchronism, but would make no provision for modulation. As will become more clear from the discussion below, in the preferred embodiment being considered, modulation is achieved by delaying the synchronizing pulse from the "lagging" disk (40 or 72) by an amount that is inversely proportional to the light input. This delay is accomplished by loading a counter-divider (divider U20 of FIG. 11 described below) with the inverse of the light value and counting this value down at a clock rate that is a near exact multiple of the sector frequency, that multiple being the equivalent of the bit width of an analog-to-digital (A/D) converter described below (A/D converter 17 of FIG. 10). Thus, for example, if ambient light is very low the output word from the A/D converter (U17) will be large and it will take longer to count down the divider (U20) thereby delaying the synchronizing pulse to the phase-locked synchronizing circuit and allowing the corresponding shutter 14 or 16 to "open."

An intra-disk synchronization circuit 136 receives position signals on lines 114 and 120 and produces left and right intershutter brake signals on lines 138 and 140, respectively.

Synchronization and modulation circuits 126 and 128, respectively, produce LEFTINBRAKE and LEFTOUTBRAKE signals on respective lines 142 and 144 and RIGHTINBRAKE and RIGHTOUTBRAKE signals on respective lines 146 and 148.

As illustrated, lines 138, 142 and 144 are connected to a left brake control unit 150 and lines 140, 146 and 148 are connected to a right brake control unit 152. Both of these units are also connected to receive, on line 154, a fast shutdown or PANIC signal from photodiode and pulsewidth modulator unit 122. The make-up of these circuits and the overall operation of the system of FIG. 5 will be considered in more detail below in connection with FIGS. 6 to 12. A pump 151 corresponding to that mentioned above includes an input, vacuum connection 153 and an output, pressure connection 155.

Figure 7:
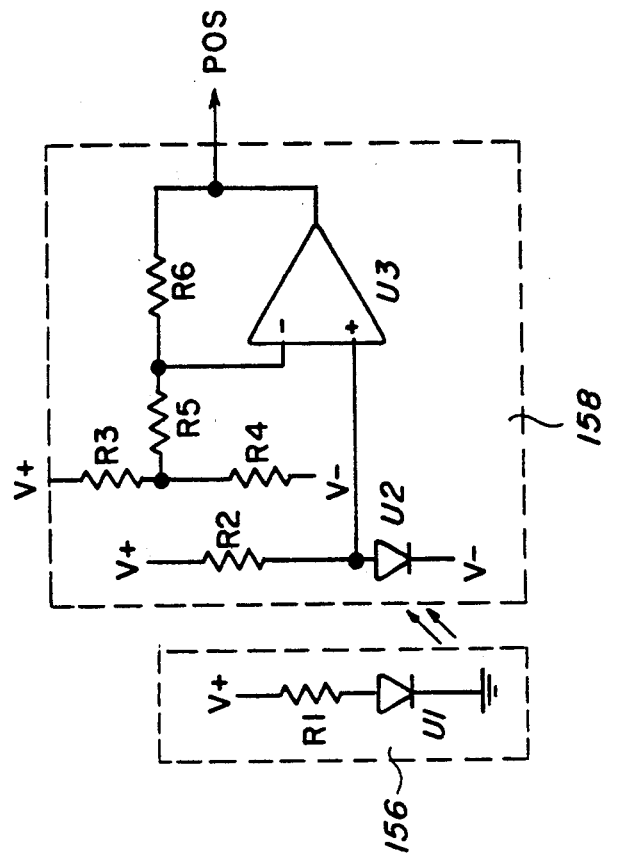
FIG. 7 is a circuit diagram of an exemplary embodiment of the photoemitter photodiode sensor of FIG. 6.
Figure 6:
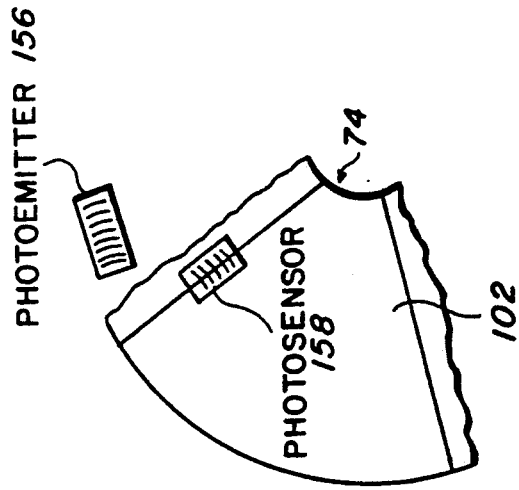
FIG. 6 is a front elevation view of a portion of the sectored disk of FIG. 4, showing the arrangement of a photoemitter and photodiode sensor used to measure sector position.

Referring to FIGS. 6 and 7, an apparatus and circuit, respectively, are shown which are used to measure the angular position of, for example, an opaque sector 102 corresponding to one of those of FIG. 4, and which in the exemplary embodiment under consideration are used in implementing the inner and outer left and right position sensors 110 and 112 (FIG. 5). A photo emitter 156 is mounted adjacent to the corresponding sectored disk 74 to provide illumination thereof and a photosensor or photodiode sensor 158 is disposed so as to receive light reflected from the disk 74.

It is assumed that the reflectivity of the sectors 102 on the sectored disk 74 is high relative to the ambient light, thus causing the light falling on sensor 158 to vary as the sectors of disk 74 pass thereunder. In the exemplary embodiment of the invention as a protection goggle, there are four such emitter-sensor pairs corresponding to emitter 156 and sensor 158 and associated with the inner and outer sectored disks 40 and 72, respectively, on both the left and right shutters. The emitter-sensor pairs on both the left and right are physically arranged such that the left and right sectored disk sets produce signals that are in phase when the two sectored disk pairs are in counterphase. In other words, when the left shutter 16 is closed and the right shutter 14 is potentially open the POS signals produced by sensors 110 and 112 (FIG. 5) are in phase with each other. Retarding the OUTPOS signal (as is explained below in connection with FIG. 12) causes the following phase-locked-loop to open the shutter 14 or 16 in direct proportion to this phase lag. While this physical arrangement holds true with both left and right shutters 16 and 14, the physical placing of the emitter-sensor pairs between shutters 14 and 16 is arranged such that the POS signals are in counterphase. Thus, taking the inner sectored disks (corresponding to disk 40) as reference points, if the left sectored disk exactly covers the viewing aperture, the right viewing aperture is exactly open and the two POS signals are exactly in phase. When the sectored disks used have an odd number of sectors as shown in the drawings, symmetrical placement of the emitter-sensor pairs on opposite sides of a vertical bisecting line (not shown) at the nasal bridge achieves this end.

Referring again to FIG. 7, photoemitter 156 includes a light emitting diode U1 which is connected in series with a resistor R1 that serves to limit the current to light emitting diode U1. Photosensor 158 includes a photodiode U2, a resistor R2 which provides bias voltage to photodiode U2, and a comparator U3. The gain of the comparator U3 is controlled by resistors R5 and R6, and the offset thereof is controlled by resistors R3 and R4. The output of photosensor 158 is a POS signal and each of the sensors 110 and 112 of FIG. 5 comprises two circuits corresponding to that of FIG. 7 so as to produce, referring back to FIG. 5, four POS signals: a LEFTINPOS signal on line 114, and a LEFTOUTPOS signal on line 116 (produced by sensors 110), and a RIGHTINPOS signal on 118 and a RIGHTOUTPOS signal on line 120 (produced by sensors 112).

Figure 8:
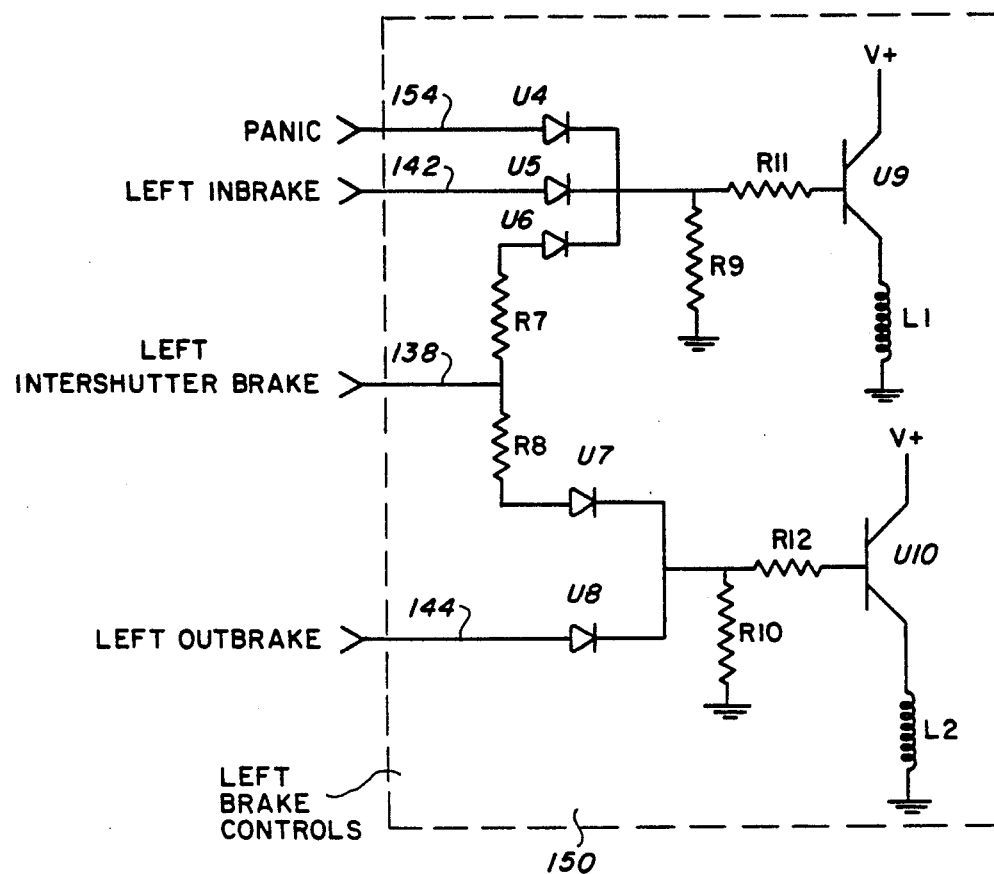
FIG. 8 is a circuit diagram of an exemplary embodiment of one of the braking control circuits of FIG. 5.

Referring to FIG. 8, there is shown a circuit diagram of a braking control circuit for controlling the protective shutters and corresponding to left brake control unit 150 of FIG. 5 (it being understood that right brake control unit 152 is substantially identical). The circuit includes a first braking coil L1 for the inner sectored disk 40 and a second braking coil L2 for the outer sectored disk 72. The driving current for coil L1 is received through a transistor U9 connected in an emitter-follower configuration that follows the current through a resistor R11. A further resistor R9 acts to hold the voltage on resistor R11 near ground when there is no incoming signal through any of three diodes U4, U5 and U6. Diodes U4, U5 and U6 form an analog OR circuit such that a rising voltage from the PANIC line 154, the LEFTINBRAKE line 142 or LEFTINTERSHUTTERBRAKE line 138 will cause the voltage across resistor R9 to increase and transistor U9 to become more conductive, thus activating coil L1. Coil L2 receives the driving current therefor through a further transistor U10 connected in an emitter-follower configuration that follows the current through a resistor R12. A further resistor R10 acts to hold the voltage on resistor R12 near ground when there is no incoming signal through diode U7 or diode U8. Diodes U7 and U8 form an analog OR circuit such that a rising voltage from the LEFTOUTBRAKE line 144 or the LEFTINTERSHUTTERBRAKE line 138 will cause the voltage across resistor R10 to increase and transistor U10 to become more conductive, thus activating coil L2. Resistors R7 and R8 are connected as shown so as to divide the LEFTINTERSHUTTERBRAKE signal on line 138 and to thus provide simultaneous braking of both inner and outer sectored disks 40 and 72.

Figure 9:
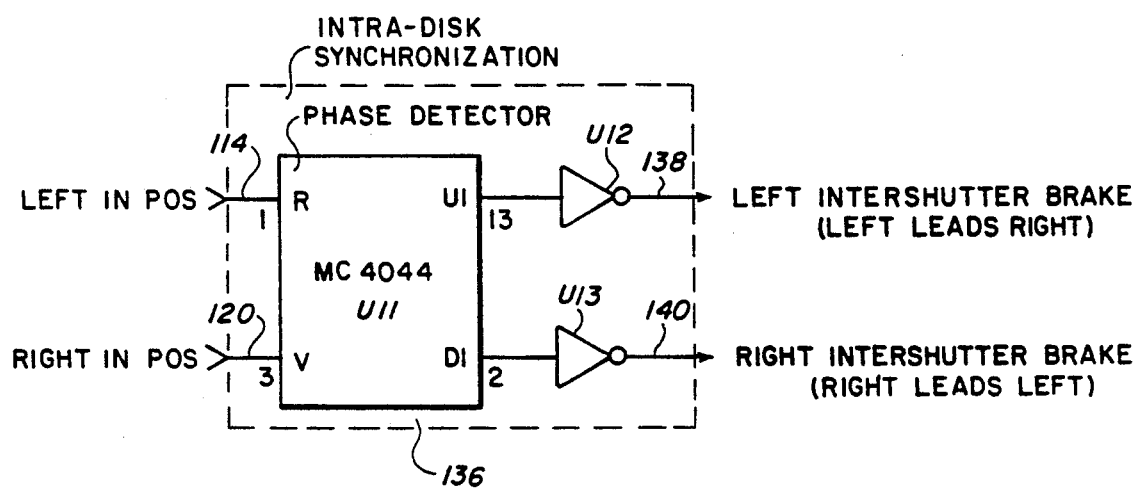
FIG. 9 is a circuit diagram of an exemplary embodiment of the intra-disk synchronization circuit of FIG. 5 which, as explained below basically comprises a phase detector used to maintain a counterphase relationship between two protective shutters of the system of the invention.

Referring to FIG. 9, there is shown a circuit diagram of an exemplary embodiment of the inter-disk synchronization circuit 136 of FIG. 5. This circuit basically comprises a phase detector circuit used to maintain a counterphase relationship between two protection shutters and comprises a MC4044 digital phase detector U11 and a pair of digital logic inverters U12 and U13 connected to the outputs of phase detector U11. The digital phase detector U11 produces two negative-going output signals that inverters U12 and U13 convert to positive logic for the braking circuit of FIG. 8. Both outputs of phase detector U11 are reflections of phase lead or lag of the incoming signals. Counterphase is maintained by the physical placement of the detectors, as discussed above.

Figure 10:
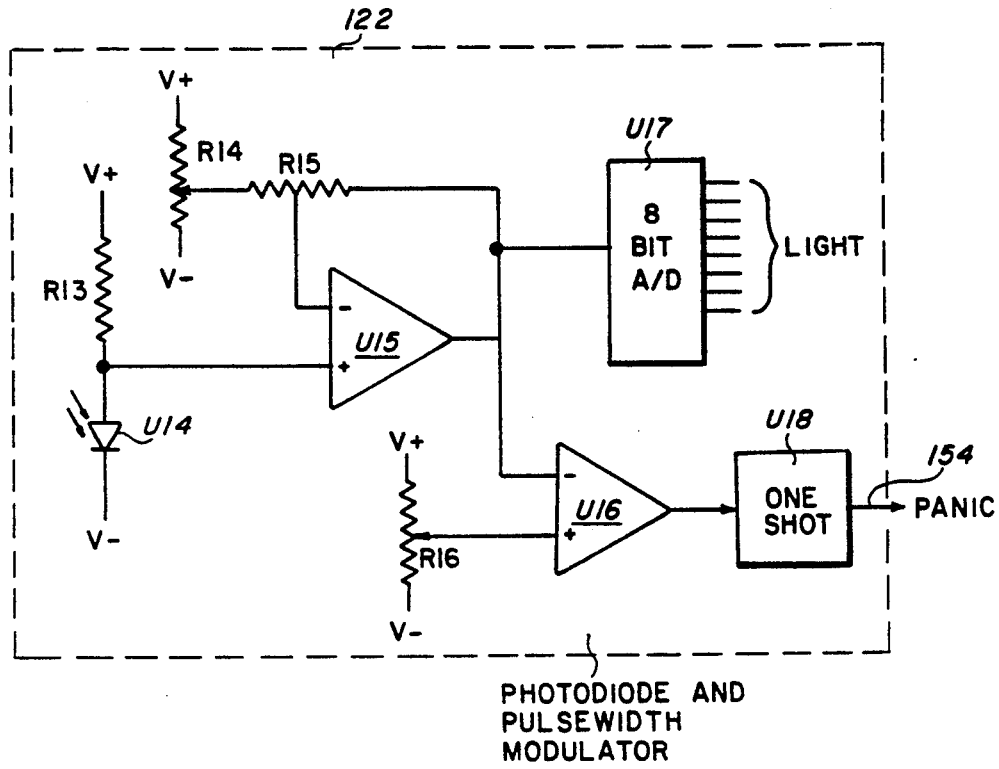
FIG. 10 is a circuit diagram of an exemplary embodiment of the photodiode and pulsewidth modulator of FIG. 5.

Referring to FIG. 10, there is shown a circuit diagram of an exemplary embodiment of photodiode and pulse width modulator circuit 122 of FIG. 5 which comprises a photodiode and binary-encoded pulsewidth modulator providing 8 bit output data words with a magnitude that is inversely proportional to light level, and a light level sensor used to indicate a dangerous level of light. As illustrated, unit 122 includes a photodiode sensor U14 connected to a resistor R13 which provides bias current for photodiode sensor U14. An operational amplifier U15 is connected to the junction between photodiode sensor U14 and resistor R13 and is controlled in gain by a potentiometer R15 and in offset by a further potentiometer R14. An analog-to-digital converter U17 is connected to the output of operational amplifier U15 and comprises an 8-bit unit that develops an output word labeled LIGHT. It is noted that the circuit in FIG. 10 is structured such that this output word is of an inverse magnitude to light magnitude. Comparator U16 has one input connected to the output of operational amplifier U15 and the other input connected to a reference resistor R16. Comparator U16 drives a one-shot multivibrator U18 to drive the PANIC output line 154 described in FIG. 5 above.

In operation, the circuit of FIG. 10 works as follows: light falling on photodiode sensor U14 causes the photodiode to become more conductive, thus lowering the voltage at the positive input terminal of operational amplifier U15. The output of operational amplifier U15 also goes low as a result, and if this voltage exceeds the setpoint voltage set by resistor R16, comparator U16 will be activated, thereby causing one-shot U18 to be triggered and the PANIC line 154 to be actuated. At the same time, A/D converter U17 is continuously updating the LIGHT signal, with the value of the LIGHT signal being in inverse relationship to the brightness of the light falling on photodiode U14.

The exact unit to be used as A/D converter U17 is not specified because a great number of A/D converters are available that could be used. Further, this circuit diagram of FIG. 10 is to be understood as being more heuristic than specific in nature. In this regard, an exact circuit diagram with specific units could be specified by any one of ordinary skill in the art.

Figure 11:
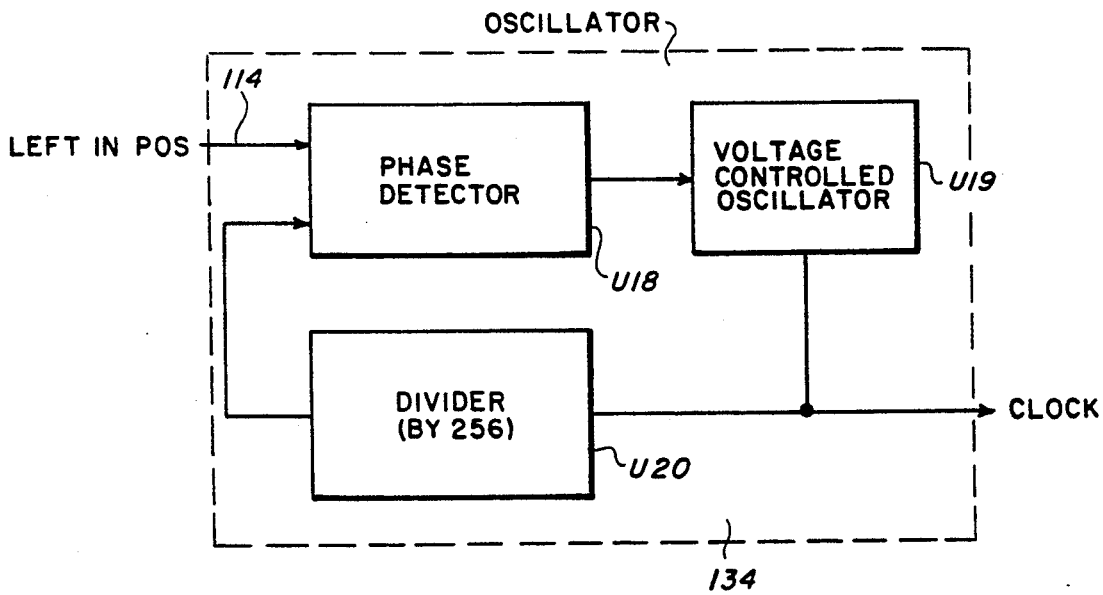
FIG. 11 is a circuit diagram of an exemplary embodiment of the oscillator circuit of FIG. 5.

Referring to FIG. 11, there is shown a circuit diagram for the clock oscillator unit or circuit 134 of FIG. 5. The clock oscillator 134 is synchronized with one disk of one protective shutter 14 or 16 and operates at a frequency that is an integer multiple of the operating frequency of all the protective shutter disks. It is noted that only one shutter disk sensor input is required to synchronize the clock oscillator 134 because all shutter disks are synchronized relative to one another, at least in the case where input light levels are static. When input levels are changing some frequency error may result for one disk relative to another, but the magnitude of this error would be quite small. FIG. 11 also shows a phase detector U18 with the LEFTINPOS signal being received from the left, inner position sensor 110 of FIG. 5 on line 114 at one input. Phase detector U18 is connected to a voltage controlled oscillator U19 the output of which is connected to a divider U20. It is assumed that the base or "free running" frequency of the clock oscillator circuit 134 is roughly 256 times the fundamental sector frequency. The effect of the divider U20, with a modulus of 256 in this case, is to reduce this output clock frequency to roughly the same frequency as the fundamental sector frequency, and the phase detector U18 can then refine this rough relationship to a near exact one. The effect of including a divider U20 in a phase-locked loop in this fashion is to make the output of the clock oscillator circuit 134 a multiple of the fundamental frequency, with that multiple being equal to the divide modulus used. It is assumed in this specific embodiment that, as stated above, the output of A/D converter U17 of FIG. 10 is an eight bit word, and thus has a range from 0 to 255, so the divide modulus of divider U20 is set as 256. Again, it is to be understood that the specific units used in implementing the circuit of FIG. 11 can be chosen from among many that are available.

Figure 12:
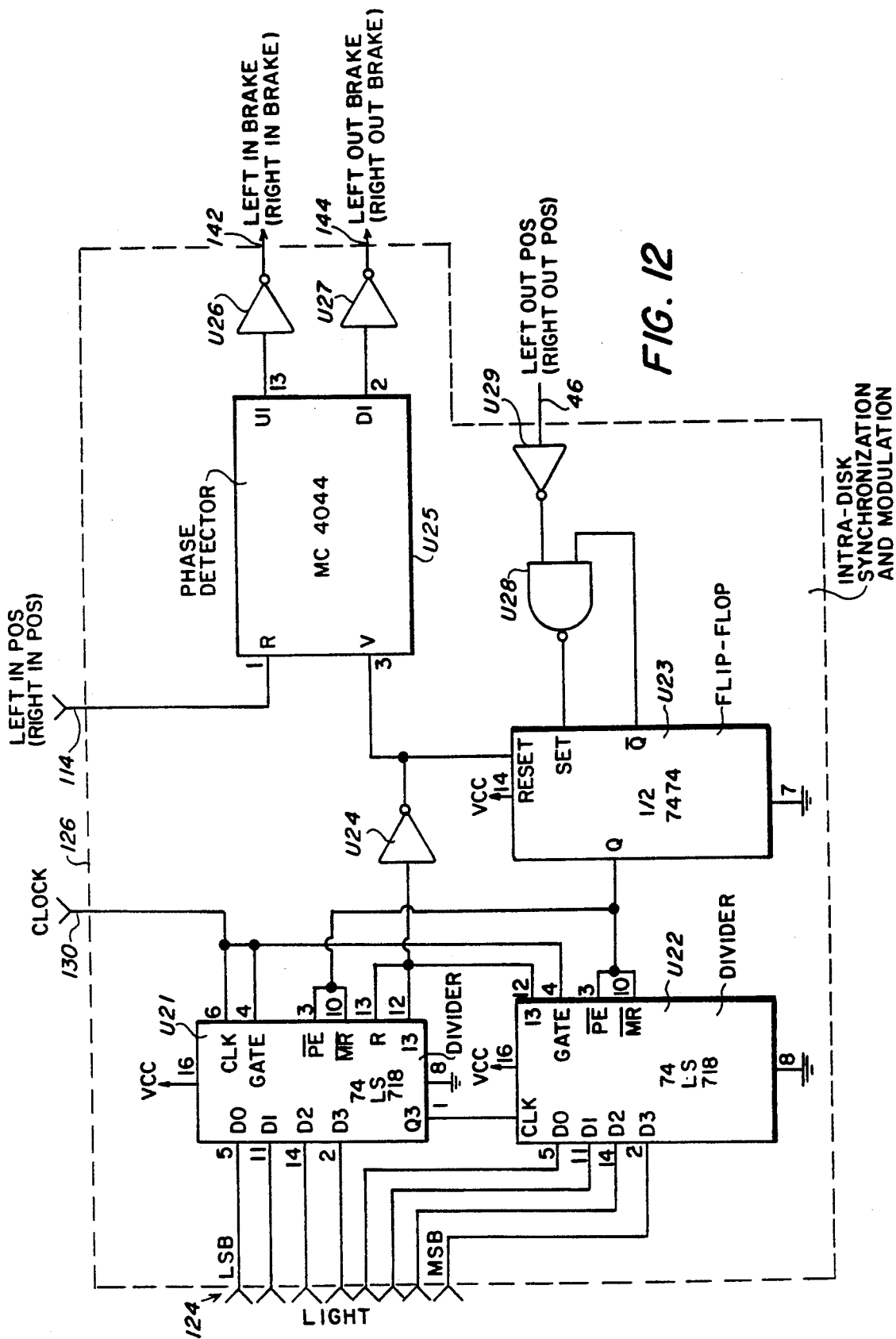
FIG. 12 is a circuit diagram of an exemplary embodiment of one of the intra-disk synchronization and modulation circuits of FIG. 5.

Referring to FIG. 12, there is shown a circuit diagram of the left intra-disk synchronization and modulation unit 126 of FIG. 5 (it being understood that the right intra-disk synchronization and modulation unit 128 of FIG. 5 is basically the same as the unit 126). The unit 126 converts the binary-encoded pulse-width of the signal from A/D converter U17 of FIG. 10 into the protective shutter opening duty cycle by delaying the synchronization of the lagging sectored disk by an amount equal to the magnitude of the LIGHT word. The unit 126 includes two modulo-divide-by-n dividers U21 and U22 that have been cascaded to provide an 8 bit word length. Dividers U21 and U22 have the LIGHT word from A/D converter U17 (line 124) as the input for the divide modulus and the CLOCK signal from oscillator unit 134 (line 130) as a clock input. It should be understood that the CLOCK frequency in 256 times that of the shutter opening frequency and, therefore, a divide modulus of 255 will "delay" the output of the divider pair U21 and U22 by a time period equal to the time it takes for one open sector to pass a point. This "delayed" output pulse is inverted by inverter U24 and split into two paths, one path going to a phase detector U25, and the other path to a reset flip-flop U23. Flip-flop U23 serves to provide signals to reset dividers U21 and U22 and initiate a count down at the beginning of the LEFTOUTPOS signal provided by left position sensors 110 on line 116 via an inverter U28 and a gate U29. Phase detector U25, which, in this exemplary embodiment, is a MC4044 phase detector, receives the other input thereto from the LEFTINPOS signal on line 114, and the outputs thereof are inverted to positive logic by inverters U26 and U27. The LEFTOUTPOS (or RIGHTOUTPOS) signal is, therefore, delayed relative to the LEFTINPOS (or RIGHTINPOS) signal by an amount proportional to the value of the LIGHT signal on line 124, thus causing the following phase-locked-loop to open, or to displace relative to each other, the shutter disks by the same proportion.

Although the exemplary embodiment of the invention described above concerns an eye-protection goggle, it will be understood that many modifications and variations of the invention are possible. For example, sensors on satellites occurring individually or as plural arrays could be likewise protected, as could sensors intended for indirect viewing as described above. It is therefore to be understood that variations and modifications can be effected in the embodiments described above without departing from the scope and spirit of the invention.

I claim:

1. Eye protection goggles for providing light protection for the eyes of a wearer, said goggles comprising:
   a pair of optical shutters adapted to be disposed in front of the eyes of a wearer; means for supporting the shutters on the face of the wearer so that the shutters are disposed in front of the eyes of the wearer; and
   a shutter control unit for controlling opening and closing of said shutters, said control unit including light detector means for detecting the light received by said optical shutters and for producing an output in accordance therewith; control means for controlling operation of said shutters such that the shutters are each opened and closed at an operating frequency sufficiently high to provide temporal integration of the light images received by the eyes of the wearer for controlling the time during each cycle of said operating frequency that the shutters are opened wherein said control means includes duty cycle control means responsive to the output of said light detector means for controlling the time during each cycle that the shutters are opened based on said output, said duty cycle control means comprises a pulse width modulator connected to said light detector for producing an output comprising pulses of a pulse width inversely related to the output of said light detector means, a voltage controlled oscillator for producing an output comprising a pulse train having a frequency which is a multiple of the operating frequency of said shutters; and
   a shutter control circuit for controlling said shutters responsive to the output of said pulse width modulation means and the output of said voltage controlled oscillator, and for providing that when one of said shutters is open, the other shutter is closed so that only one eye of the wearer is exposed at any one time; and override means, responsive to the output of said light detecting means, for providing that said shutters are both closed when said output exceeds a predetermined value and
   wherein said optical shutters each comprise a pair of coaxial rotatable disks each including alternating opaque and transparent sectors, said duty cycle control means further comprises shutter position sensing means for sensing the position of the disks of said shutters and for producing a corresponding output signal, and wherein said shutter control circuit is also responsive to the output signal produced by said shutter position sensing means in controlling said shutters.

2. Eye protection goggles as claimed in claim 1 further comprising braking means for providing braking of disks and mechanical synchronizing means for limiting deviation in phase between the rotatable disks during rotation of said disks and for ensuring that when a disk of leading phase relative to other disk of said pair of disks is braked, said other disk of said pair of disks will overlap the disk of leading phase to provide closing of said shutter.

3. Eye protection goggles as claimed in claim 2 wherein said mechanical synchronizing means comprise interdigitizing tabs providing loose interdigitation between said disks.

4. Light protection apparatus for an optical sensing element or elements such as the eyes or another optical sensor or sensors, said apparatus comprising:
- at least one optical shutter for protecting a corresponding optical sensing element, the number of optical shutters being equal to the number of sensing elements to be protected, at least one shutter comprised of a pair of coaxial rotatable disks each including alternating opaque and transparent sectors mechanical synchronizing means connected between said rotatable disks for limiting the deviation in phase between the disks during rotation of the disks; and
- a shutter control apparatus for controlling opening and closing of said at least one shutter so as to control the light admitted to said corresponding optical sensing element, said shutter control apparatus comprising light detector means for sensing the level of the light falling on said at least one shutter and for producing an output in accordance therewith; control means for controlling the operation of said at least one shutter such that the shutter is cyclically opened and closed at a operating frequency sufficiently high to provide integration of the light on the sensor being protected and for, responsive to the output of said light detector means, controlling the time during each cycle of said operating frequency that the shutter is opened based on the light level senses; said control means further including override means responsive to the output of said light detector means for providing closing of said shutter when the light level sensed exceeds a predetermined level wherein said mechanical synchronizing means comprises interdigitizing tabs providing loose interdigitation between the disks.

5. Light protection apparatus as claimed in claim 4 further comprising braking means controlled by said control means for braking rotation of said disks, said control means including means for providing differential braking of said disks to maintain a desired phase relation between said disks.

6. Eye protection goggles for providing light protection for the eyes of a wearer, said goggles comprising:
- a pair of optical shutters adapted to be disposed on front of the eyes of a wearer said shutters each comprise a pair of coaxial rotatable disks each including alternating opaque and transparent sectors further comprising mechanical synchronizing means connected between said rotatable disks for limiting the deviation in phase between the disks, during rotation of the disks;
- means for supporting the shutters on the face on the wearer so that the shutters are disposed in front of the eyes of the wearer; and
- a shutter control unit for controlling opening and closing of said shutters, said control unit including control means for controlling operation of said shutters such that the shutters are each opened and closed at an operating frequency sufficiently high to provide temporal integration of the light images received by the eyes of the wearer, and for providing that when one of said shutters is open, the other shutter is closed so that only one eye of the wearer is exposed at any one time, light detector means for detecting the light received by said optical shutters and for producing an output in accordance therewith and wherein said control means further comprises override means, responsive to the output of said light detector means, for providing that said shutters are both closed when said output exceeds a predetermined value said control means further comprises duty cycle control means responsive to the output of said light detecting means for controlling the time during each cycle that said shutters are opened based on said output said duty cycle control means comprises a pulse width modulator connected to said light detector for producing an output comprising pulses of a pulse width inversely related to the output of said light detector means, a voltage controlled oscillator for producing an output comprising a pulse train having a frequency which is a multiple of the operating frequency of said shutters; and a shutter control circuit for controlling said shutters responsive to the output of said pulse width modulation means and the output of said voltage controlled oscillator.

7. Eye protection goggles as claimed in claim 6 further comprising braking means controlled by said control means for braking rotation of said disks, said control means including means for providing differential braking of said disks to maintain a desired phase relation between said disks.

8. Eye protection goggles as claimed in claim 6, wherein said optical shutters each comprise a pair of coaxial rotatable disks each including alternating opaque and transparent sectors said duty cycle control means further comprises shutter position sensing means for sensing the position of the disks of said shutters and for producing a corresponding output signal, and wherein said shutter control circuit is also responsive to the output signal produced by said shutter position sensing means in controlling said shutters.

9. Eye protection goggles as claimed in claim 8 further comprising braking means for providing braking of disks and mechanical synchronizing means for limiting deviation in phase between the rotatable disks during rotation of said disks and for ensuring that when a disk of leading phase relative to other disk of said pair of disks will overlap the disk of leading phase to provide closing of said shutter.

10. Eye protection goggles as claimed in claim 9 wherein said mechanical synchronizing means comprise interdigitizing tabs providing loose interdigitation between said disks.

* * * * *